United States Patent
Bhide et al.

(10) Patent No.: US 10,245,271 B2
(45) Date of Patent: Apr. 2, 2019

(54) TREATMENT OF IMPAIRED COGNITIVE FLEXIBILITY WITH TRKB RECEPTOR ANTAGONISTS

(71) Applicants: Florida State University Research Foundation, Inc., Tallahassee, FL (US); The General Hospital Corporation, Boston, MA (US)

(72) Inventors: Pradeep G. Bhide, Tallahassee, FL (US); Dierdre M. McCarthy, Tallahassee, FL (US); Joseph Biederman, Brookline, MA (US); Thomas J. Spencer, Carlisle, MA (US)

(73) Assignees: Florida State University Research Foundation, Inc., Tallahassee, FL (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/215,327

(22) Filed: Jul. 20, 2016

(65) Prior Publication Data

US 2017/0020888 A1    Jan. 26, 2017

Related U.S. Application Data

(60) Provisional application No. 62/194,439, filed on Jul. 20, 2015.

(51) Int. Cl.
| | |
|---|---|
| *A61K 31/00* | (2006.01) |
| *A61K 38/00* | (2006.01) |
| *A61K 31/70* | (2006.01) |
| *A61K 31/66* | (2006.01) |
| *A61K 31/551* | (2006.01) |
| *A61K 38/06* | (2006.01) |
| *A61K 31/55* | (2006.01) |
| *A61K 38/12* | (2006.01) |

(52) U.S. Cl.
CPC ............ *A61K 31/551* (2013.01); *A61K 31/55* (2013.01); *A61K 38/06* (2013.01); *A61K 38/12* (2013.01)

(58) Field of Classification Search
None
See application file for complete search history.

(56) References Cited

U.S. PATENT DOCUMENTS

| 9,623,023 B2 * | 4/2017 | Bhide .................. A61K 31/485 |
|---|---|---|
| 2014/0088119 A1 | 3/2014 | Messer et al. |

OTHER PUBLICATIONS

Heled et al, J. Clin. Exp. Neuropsycol, 2014, 34(2):151-9.*
Correia et al., Genes, Brain and Behavior, 2010, 9:841-8.*
DSM-5, American Psychiatric Publishing, 2013, p. 55.*
Maxime Cazorla, Anne Jouvenceau, Christiane Rose, Jean-Philippe Guilloux, Catherine Pilon, Alex Dranovsky, Joel Premont; "Cyclotraxin-B the First Highly Potent and Selective TrkB Inhibitor, Has Anxiolytic Properties in Mice;" PLos One; vol. 5, Issue 3; Mar. 2010.
Maxime Cazorla, Joel Premont, Andre Mann, Nicolas Girard, Christoph Kellendonk, Didier Rognan; "Identification of a Low-Molecular Weight TrkB Antagonist with Anxiolytic and Antidepressant Activity in Mice"; The Journal of Clinical Investigation, vol. 121, No. 5, May 2011.

* cited by examiner

*Primary Examiner* — Olga N Chernyshev
(74) *Attorney, Agent, or Firm* — Christopher M. Ramsey; GrayRobinson, P.A.

(57) ABSTRACT

The cognitive flexibility of a subject may be improved by administering a therapeutically effective amount of a TrkB receptor antagonist to the subject in need thereof. The TrkB receptor antagonist compound may be administered in a pharmaceutical dosage form.

7 Claims, 3 Drawing Sheets

TREATMENT OF IMPAIRED COGNITIVE FLEXIBILITY WITH TRKB RECEPTOR ANTAGONISTS

CROSS-REFERENCE TO RELATED APPLICATION

This claims priority to U.S. provisional Application No. 62/194,439, filed Jul. 20, 2015, which is hereby incorporated by reference in its entirety.

FIELD

This relates to the field of treating cognitive impairment and, more particularly, to treating cognitive inflexibility.

BACKGROUND

Cognitive flexibility is the ability to execute multiple mental tasks simultaneously, to switch from one task to the next easily, and restructure knowledge and strategy to tackle changing tasks. It has been described as the mental ability to control what one is thinking about, how one is thinking about it, and to change one's mind about it. Normal or physiological cognitive flexibility is demonstrated by an animal when it is required to change its thinking about a subject in response to a new set of rules, requiring the animal to perform a previously learned task under a new set of rules sometimes in a new environment.

There are many different factors that affect one's cognitive flexibility. Cognitive flexibility may be impaired by psychiatric conditions, aging, exposure to drugs or other toxins, and addiction. Impaired cognitive flexibility has been demonstrated in some people with ADHD, OCD, autism spectrum, Asperger's syndrome, schizophrenia, and anorexia-nervosa, for example. When cognitive flexibility is impaired, this is referred to as "cognitive inflexibility."

Despite its important role in normal mental function, and its well-documented impairment, drugs that selectively target and improve cognitive flexibility are not readily available. The actions of the neurotransmitters dopamine, glutamate and GABA in multiple brain regions including the frontal cortex and basal ganglia are important regulators of cognitive flexibility and could be involved in the pathogenesis of cognitive inflexibility.

SUMMARY

Cognitive flexibility may be treated with a tyrosine kinase B (TrkB) receptor antagonist because excess signaling by brain derived neurotrophic factor (BDNF) via TrkB is associated with impaired cognitive flexibility.

A method of treating impaired cognitive flexibility includes administering to a subject having impaired cognitive flexibility a therapeutically effective amount of a selective TrkB receptor antagonist compound.

A pharmaceutical composition for treating cognitive inflexibility, includes a pharmaceutical dosage form having therein a therapeutically effective amount of a selective TrkB receptor antagonist compound blended with a pharmaceutical carrier.

A method of making the pharmaceutical composition includes combining into a pharmaceutical dosage form a therapeutically effective amount of a selective TrkB receptor antagonist compound and a pharmaceutical carrier.

The therapeutically effective amount is an amount sufficient to improve cognitive flexibility in the subject.

The TrkB receptor antagonist compound may be at least one compound selected from (a) ANA-12, an (b) ANA-12 based compound, and (c) a pharmaceutically acceptable salt of compound (a) or (b).

The TrkB receptor antagonist compound may be at least one compound selected from (a) cyclotraxin-B, (b) a cyclotraxin-B based compound, and (c) a pharmaceutically acceptable salt of compound (a) or (b).

The TrkB receptor antagonist compound may be at least one compound selected from (a) N-T04, (b) an N-T04 based compound, and (c) a pharmaceutically acceptable salt of compound (a) or (b).

The TrkB receptor antagonist compound may be least one compound selected from (a) N-T19, (b) an N-T19 based compound, and (c) a pharmaceutically acceptable salt of compound (a) or (b).

The TrkB receptor antagonist compound may be selective for inhibiting TrkB.

The TrkB receptor antagonist compound may be selective such that it does not inhibit TrkA or TrkC.

DETAILED DESCRIPTION OF EXAMPLE EMBODIMENTS

Figure 1A:
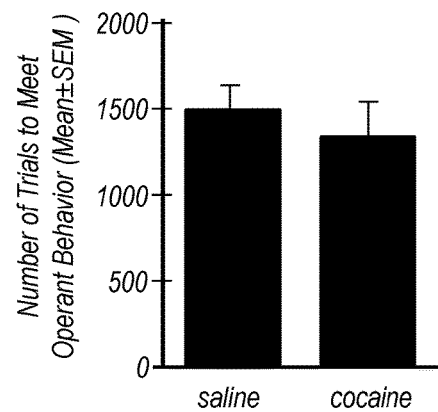
FIG. 1A is a bar graph comparison of the number of trials it took prenatally saline- and cocaine-exposed mice to meet operant behavior.

This disclosure describes example embodiments, but not all possible embodiments of the compositions and methods. Where a particular feature is disclosed in the context of a particular embodiment, that feature can also be used, to the extent possible, in combination with and/or in the context of other embodiments. The methods and compositions may be embodied in many different forms and should not be construed as limited to only the aspects and examples described here.

Excess signaling by brain derived neurotrophic factor (BDNF) via its receptor tyrosine kinase B (TrkB) is associated with impaired cognitive flexibility. Cognitive flexibility may be improved by administering a TrkB receptor antagonist compound.

A TrkB receptor antagonist may be used to treat impaired cognitive flexibility. An example of a method of treatment includes administering to a subject having impaired cognitive flexibility a therapeutically effective amount of a TrkB receptor antagonist for improving cognitive flexibility in the subject.

An example of a TrkB receptor antagonist is ANA-12, more formally named N-[2-[[(Hexahydro-2-oxo-1H-azepin-3-yl) amino]carbonyl]phenyl]-benzo[b]thiophene-2-carboxamide, which has the formula shown below.

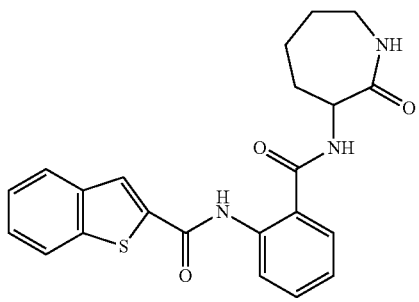

ANA-12

ANA-12 is a TrkB ligand that inhibits activation of the receptor by BDNF. It binds selectively to TrkB and inhibits processes downstream of TrkB without substantially altering TrkA and TrkC functions. Through ANA-12 treatment, a statistically significant number of subjects tested showed improved cognitive flexibility. In adult mouse models, ANA-12 has also been shown to decrease TrkB activity in the brain without affecting neuronal survival. Mice dosed with ANA-12 have shown reduced anxiety- and depression-related behaviors according to Cazorla et al., in J. Clin. Invest. 121(5), pages 1846-57 (2011).

The TrkB receptor antagonist does not necessarily have to be ANA-12 itself. ANA-12 may serve as a lead compound for ANA-12 based derivatives, which may have additional functional groups added to the ANA-12 structure. The ANA-12 derivatives may be functionalized, for example, with functional groups not limited to alkane, alkene, alkyne, alkyl halide, alcohol, ether, ester, amine, amide, aldehyde, ketone, or carboxylic acid, among others. Such ANA-12 derivatives are referred to here as ANA-12 based compounds.

Other examples of TrkB receptor antagonists that may be used include, but are not limited to cylcotraxin-B, N-T04 and N-T19. Derivatives of cylcotraxin-B, N-T04 and N-T19, which are referred to here as cylcotraxin-B based compounds, N-T04 based compounds, and N-T19 based compounds may also be used. Pharmaceutically acceptable salts of the TrkB receptor antagonists and/or their derivatives may also be used.

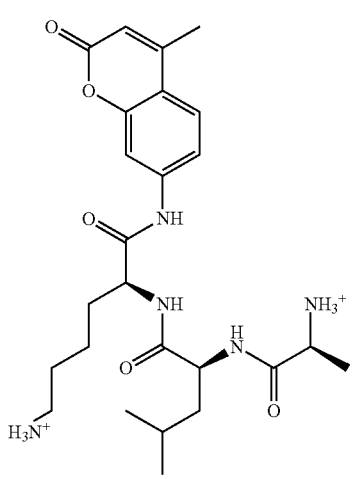

N-T04

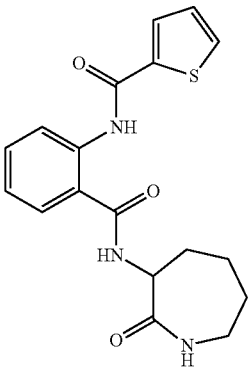

N-T19

Cyclotraxin-B (PubChem CID 90489002) is a cyclic peptide with the formula $C_{48}H_{73}N_{13}O_{17}S_3$. The IUPAC name of cyclotraxin-B is (3S,6R,11R,17S,20S,26S,32S,35S)-6-amino-20-(4-aminobutyl)-3-(2-amino-2-oxoethyl)-17-(2-carboxyethyl)-23-[1R)-1-hydroxyethyl]-26-[(4-hydroxyphenyl)methyl]-32-(2-methylsulfanylethyl)-2,5,13,16,19,22,25,28,31,34-decaoxo-8,9-dithia-1,4,12,15,18,21,24,27,30,33-decazabicyclo[33.3.0]octatriacontane-11-carboxylic acid.

The TrkB receptor antagonist compound may be selective for inhibiting or binding to TrkB receptors. This means that the TrkB receptor antagonist compound does not substantially also inhibit or bind to TrkA or TrkC receptors.

The TrkB receptor antagonist compound may be administered as an active ingredient in a pharmaceutical composition. In such a case, the TrkB receptor antagonist may be blended with one or more ingredients useful for making the composition into a pharmaceutically acceptable dosage form such as a suspension, tablet, capsule, injectable, dermal patch, or other dosage form.

The term "pharmaceutical composition" means a pharmaceutical product that includes at least one therapeutically effective ingredient combined with inert pharmaceutically acceptable excipients or carriers into a pharmaceutical dosage form. A "pharmaceutically acceptable" ingredient in the composition is an ingredient that is compatible with the other ingredients in the composition and is recognized as being acceptable for pharmaceutical use.

The pharmaceutical composition may include the TrkB receptor antagonist compound, TrkB receptor antagonist-based compound, a pharmaceutically acceptable salt of the TrkB receptor antagonist compound or TrkB receptor antagonist-based compound, or a combination thereof.

Exemplary ingredients that may be included in the pharmaceutical composition include one or more excipients, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

There are many different ways that TrkB receptor antagonists may be administered to the subject. These administration techniques include, but are not limited to administering one or more pharmaceutically acceptable dosage forms such as suspensions, tablets, suppositories, capsules, injectables, transdermals or the like. Other suitable administration techniques include oral, sublingual, buccal, intravenous, subcutaneous, transcutaneous, intramuscular, intracutaneous, intrathecal, epidural, intraocular, intracranial, inhalation, intranasal, or the like. Any combination of administration techniques may also be used.

The excipients used in the composition may vary depending on the type of dosage form and administration technique. If the dosage form is a pill, for example, the excipients may be in granular or powder form. If the dosage form is a liquid, the excipients may be in liquid form.

The pharmaceutical composition may be prepared by combining into the pharmaceutical dosage form the therapeutically effective amount of the TrkB receptor antagonist compound and a pharmaceutical carrier. This may be achieved by blending the TrkB receptor antagonist compound and pharmaceutical carrier together, then shaping or packaging the combination into the desired final dosage form.

The therapeutically effective amount is at least the minimum amount that provides the intended therapeutic effect on the subject treated. In humans, an effective amount range is often 1-1,000 mg/day, including 1-25 mg/day, 25-50 mg/day, 50-75 mg/day, 75-100 mg/day, 100-150 mg/day, 150-200 mg/day, 200-250 mg/day, 250-300 mg/day, 300-350 mg/day, 350-400 mg/day, 400-450 mg/day, 450-500 mg/day, 500-550 mg/day, 550-600 mg/day, 600-650 mg/day, 650-700 mg/day, 700-750 mg/day, 750-800 mg/day, 800-850 mg/day, 850-900 mg/day, 900-950 mg/day, 950-1,000 mg/day. Higher doses (1,000-3,000 mg/day) might also be effective.

By way of example, in terms of effective amount by body weight, an effective amount may be about 0.001 mg/kg to about 20 mg/kg; about 5 mg/kg to about 15 mg/kg; about 1 mg/kg to about 5 mg/kg body weight; about 0.1 mg/kg to about 1 mg/kg; 0.01 mg/kg to about 0.1 mg/kg; about 0.001 mg/kg to about 0.01 mg/kg; or about 0.001 to about 0.05 mg/kg.

By way of example, the therapeutically effective amount of the TrkB receptor antagonist compound in the pharmaceutical composition may be a dose of about 0.1 mg, about 1 mg, about 2 mg, about 2.5 mg, about 5 mg, about 10 mg, about 15 mg, about 20 mg, about 25 mg, about 30 mg, about 40 mg, about 45 mg, about 50 mg, about 60 mg, about 80 mg, about 100 mg, or about 200 mg. The pharmaceutical composition may be administered once daily or multiple times daily.

The therapeutically effective amount may vary depending on numerous factors, including age, weight, height, severity of the disorder, administration technique, and others. The actual amount of TrkB receptor antagonist to be administered in a given case may be determined by a physician taking into account the relevant circumstances. The amounts provided above are given as possible examples. In practice, the actual amount of TrkB receptor antagonist that is administered to a subject may fall below or above these amounts, depending on the subject's needs.

The pharmaceutical composition may include a stimulant or a non-stimulant compound effective in the treatment of attention deficit in order to treat conditions that exhibit cognitive inflexibility and attention deficits, such as Asperger's syndrome, autism spectrum, or ADHD. An example of such a stimulant compound is methylphenidate.

The pharmaceutical composition may be administered as part of a dose regimen that includes varying changes in the dose during the treatment period.

If the pharmaceutical composition includes a solution containing the TrkB receptor antagonist, the TrkB receptor antagonist concentration may be, for example, about 0.01 $\mu$M to about 1,000 $\mu$M, about 1 $\mu$M to about 500 $\mu$M, about 25 $\mu$M to about 175 $\mu$M, about 50 $\mu$M to about 150 $\mu$M, or about 75 $\mu$M to about 125 $\mu$M.

The solution may be in an injectable pharmaceutical dosage form such as a syringe or intravenous (IV) fluid bag.

A subject, as used herein, refers to an animal such as a human or otherwise that is being treated with the pharmaceutical composition.

The subject's impaired cognitive flexibility may be the result of a psychiatric condition, aging, exposure to drugs or other toxins, and/or addiction. As mentioned above, impaired cognitive flexibility has been demonstrated in some people with ADHD, OCD, autism spectrum, Asperger's syndrome, schizophrenia, and anorexia-nervosa, for example. The TrkB receptor antagonist compound may be used to treat impairment of cognitive flexibility in subjects having any of these types of conditions.

One of the ways impaired cognitive flexibility may be manifested or assessed is through impaired reversal learning. Reversal learning is a situation in which a subject is trained to respond differentially to two stimuli under positive or negative reinforcement conditions and is subsequently trained under reversed reinforcement conditions. A TrkB receptor antagonist may improve reversal learning in subjects having impaired cognitive flexibility.

The cognitive flexibility of a human subject can be measured in a psychiatric evaluation by employing conventional tests such as two subtests from the Delis-Kaplan Test of Executive Functioning, including: 1) Letter-Number switching from the Trail making subtest and 2) Inhibition/Switching condition of the Color Word Interference Test. The test is described by Heled, et al. in J. Clin. Exp. Neuropsychol, 34(2), pgs. 151-9 (2014), which is incorporated by reference herein.

EXAMPLE

This example section is provided to further illustrate certain aspects of the composition and methods. The scope of the claims is not limited to only what these examples teach.

This example shows that prenatal cocaine exposure produced persistent impairments in reversal learning in a mouse model and that a TrkB receptor antagonist compound may improve cognitive flexibility.

A. Development of a Mouse Model for Testing the Efficacy of the TrkB Receptor Antagonist Compound Swiss Webster mice were housed in a temperature and humidity controlled environment on a 12 hr light/dark cycle with food and water available ad libitum were bred to obtain timed pregnancies.

The day of vaginal plug detection was considered embryonic day 0 (E0) and the day of birth postnatal day 0 (P0). Pregnant dams of comparable body weight were assigned to saline or cocaine exposure groups on the 6th day of pregnancy.

Singly housed dams received twice daily (7 AM and 7 PM) subcutaneous injections of cocaine (20 mg/kg/injection: total daily dose=40 mg/kg/day) or saline (same volume and time of administration as the cocaine injection) from the 8th day of pregnancy until the day of birth. The period of cocaine exposure corresponds to mid-first trimester of human pregnancies.

The offspring from both the groups were cross-fostered to drug naïve dams within 2 days of birth to eliminate potential effects of the experimental interventions on mother-infant interactions. Although food consumption by the cocaine exposed dams is reduced compared to that of the saline-exposed dams, the developmental, anatomical, biochemical or behavioral phenotypes observed in the prenatally cocaine exposed offspring are due to the effects of cocaine and not nutritional factors. Therefore, to avoid unnecessary use of laboratory animals, we did not include nutritional controls. All offspring were weaned on P21.

The experimental procedures were in compliance with institutional guidelines at Florida State University and the NIH Guide for the Care and Use of Laboratory Animals. No more than 2-3 mice from any given litter were used in the experimental analyses described below, and 3-4 litters were used from each prenatal treatment condition and for each set of studies.

B. Behavioral Testing of Mouse Model Subjects

The mice were housed 2-4 per cage and were handled for at least one week prior to the beginning of the analyses at P60. Mice were habituated to the testing room for at least 30 min prior to testing. The behavioral analyses were performed during the lights-off period.

Olfactometry: Reversal learning was assayed in an automated olfactometer based on odor learning and detection using water as reward (41, 42). Briefly, odorants were presented via an 8-channel liquid dilution computerized olfactometer (Knosys LD8-1, Tampa, Fla.) so that odorant threshold determinations were automated and stimulus concentration, timing of onset and offset, and stimulus control of behavior could be controlled reliably. We modified our Knosys system to provide additional mechanical dampening of the solenoid pinch valves to permit incorporation of materials for mounting the machine in-line with sterilization of the olfactometer.

The Knosys olfactometer employs operant conditioning in the form of both positive and negative reinforcements. Positive reinforcement is used when pairing an odorant with water reward (S+). A 10-second time out or negative reinforcement occurs as a result of a mouse responding to a negative cue or diluent (S−). Mice were therefore trained in a classical "go no-go" operant conditioning paradigm to recognize an odorant.

Operant training: Mice were water-deprived to 85% of their baseline bodyweight to motivate them for a water reward. Operant training was performed using a step-wise battery of tasks that began with reward reinforcement for learning to lick a water delivery tube and snout insertion into the odor sampling port. Mice advanced to the next stage after 30 reinforcements. Next, mice were reinforced for lick decisions paired with a positively entrained odor (S+). They were required to nose poke for an extended period of time to sample an odor prior to receiving water reinforcement. The sampling time was progressively increased from 0-1 sec. over 119 trials and mice had to successfully complete four consecutive trials over a two-day period to advance to the go no-go operant training.

During the go no-go operant training mice inserted their snout into the odor sampling port to initiate a trial and waited until the odor stimulus was presented. The mouse sampled the stimulus and then responded or did not respond, depending on the type of stimulus presented. The mice were rewarded for lick decisions paired with a positively entrained odor (S+) and also for correct rejections paired with a negatively entrained odor (S−). This establishes the "go no-go" reward criteria. The percentage of correct responses per trial was determined by the formula: % correct responses=[(HITs+Correct Rejections)/20]×100, where a HIT is defined as a criterion response in the presence of S+, and a Correct Rejection (CR) is a failure to make a criterion response in the presence of S+ and 20 represents the number of trials per block.

Discrimination training: Initially the mice were challenged with a simple discrimination between odor (S+) vs. diluent (S−) and following acquisition of 80% correct decisions (defined criteria), they were transitioned to two-odor discrimination testing, or odor 1 (S+) vs. odor 2 (S−).

Odor Reversal Learning: Once mice achieved criteria performance on the two-odor discrimination testing for a week, mice underwent an odor-reversal learning paradigm. Here mice were introduced to the switch (reversal) of the S+ for the S− stimulus where the previously rewarded odor stimulus now lacked the water reward and the previously unrewarded odor stimulus was now paired with the water reward.

The scent stimuli used were 5% Ethyl Acetate (EA) and 1% Acetophenone (AP).

C. Administration the TrkB Receptor Antagonist Compound ANA-12 to Mouse Model Subjects Upon successful completion of the training phase and odor discrimination phase a subset of mice were randomly assigned to the ANA-12 injection group. ANA-12 (Sigma Aldrich, St. Louis, Mo.; SML0209) was administered twice daily [0.5 mg/kg; 1.0 mg/kg/day intraperitoneal (i.p.)] for 13 consecutive days. ANA-12 was dissolved in 100% DMSO (stock), and diluted further such that the final concentration of DMSO administered to the mice was 1%. On days 8-10 of the injection period, the mice were water deprived (to 85% of pre-deprivation weight). On the 11th day, the mice were returned to the operant chamber 2 hours after the morning injection and re-tested for their ability to discriminate between the S+ and S− odors.

On day 12 odors were reversed and the % of correct responses was recorded (day 1 reversal learning). If the mice did not reach 80% criteria, they were then presented with an additional 200 trials on day 13 (day 2 reversal learning).

Differences among the prenatal treatment groups, between male and female mice within a group, and the interaction between prenatal treatment and sex were analyzed using a two-way analysis of variance (ANOVA). Post-hoc pair-wise comparisons were performed using a Bonferroni correction. A two-tailed Student's t-test was used when differences between only two groups were analyzed. A Mann-Mann-Whitney's U test was used to examine the impact of ANA-12 injections in a population of mice in two treatment groups.

C. Olfactory Reversal Learning Deficits in Prenatally Cocaine-Exposed Offspring

The mice were trained in a go no-go operant-conditioning paradigm to associate a specific odor with water reward. There was no significant difference in operant training (number of trials required to associate odor with the reward) between the prenatally saline- or cocaine-exposed mice (Student's t-test; Mean±SEM: saline: 1500±143, cocaine: 1340±204, t=0.640, df=18, p>0.05, FIG. 1A).

Figure 1B:
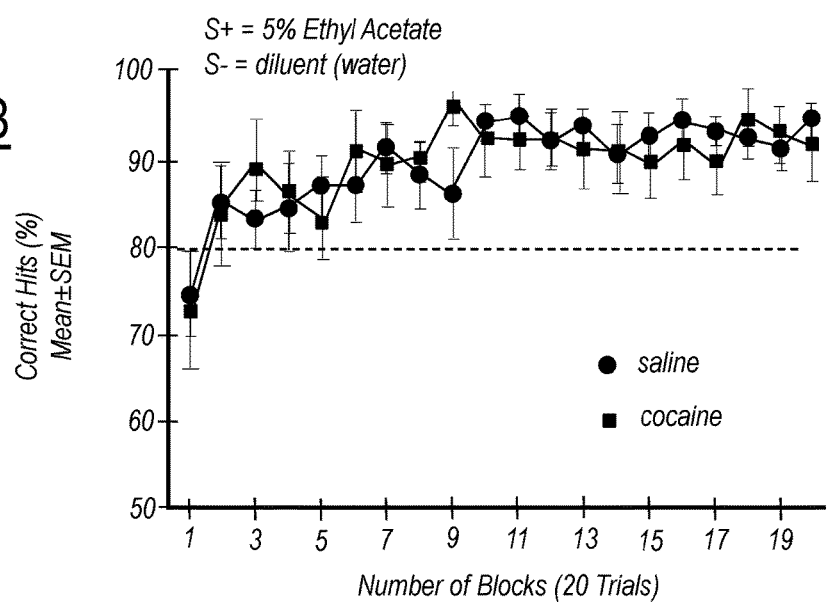
FIG. 1B is a line graph comparison of the percentage of correct hits for odor vs. diluent discrimination for prenatally saline- and cocaine-exposed mice.

Olfactory performance was compared using a simple discrimination task in which mice were tested for their ability to discriminate between 5% EA (S+) and a diluent (water; S−). Prenatally saline- or cocaine-exposed mice were equally able to discriminate between the odor and diluent (two-way ANOVA; $F_{(1,329)}$=0.077, p>0.05, FIG. 1B).

Figure 1C:
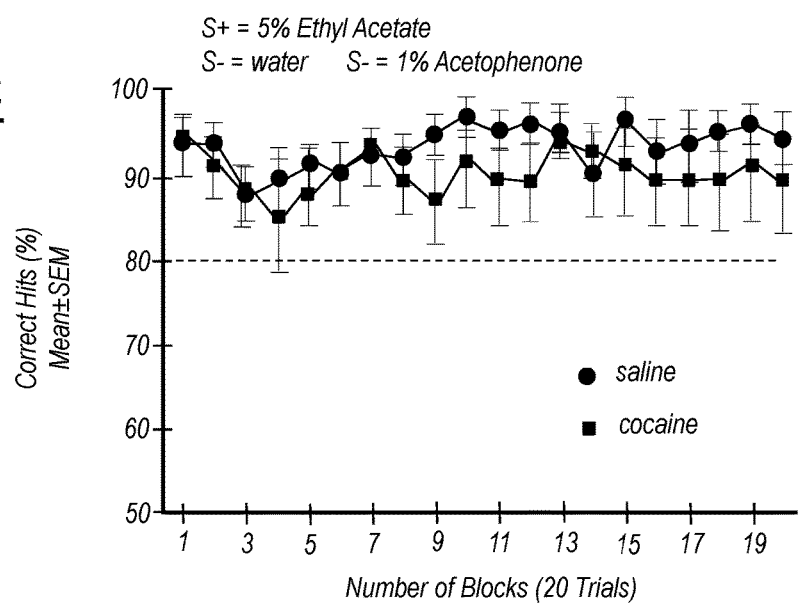
FIG. 1C is a line graph comparison of the percentage correct hits for odor vs. odor discrimination for prenatally saline- and cocaine-exposed mice continue to perform above criteria (dashed line=80% correct hits).

Next, the mice were tested for their ability to discriminate between two odors, one of which (5% EA) would result in a water reward (S+) and the other (1% AP) with no reward (S−; odor versus odor discrimination). Mice from both the prenatal treatment groups performed this task equally well, remained above the 80% correct hit criteria, and continued to perform at this level for the remainder of the trials (Main effect of treatment: two-way ANOVA; $F_{(1,10)}=0.53$, $p>0.05$, FIG. 1C).

Figure 2A:
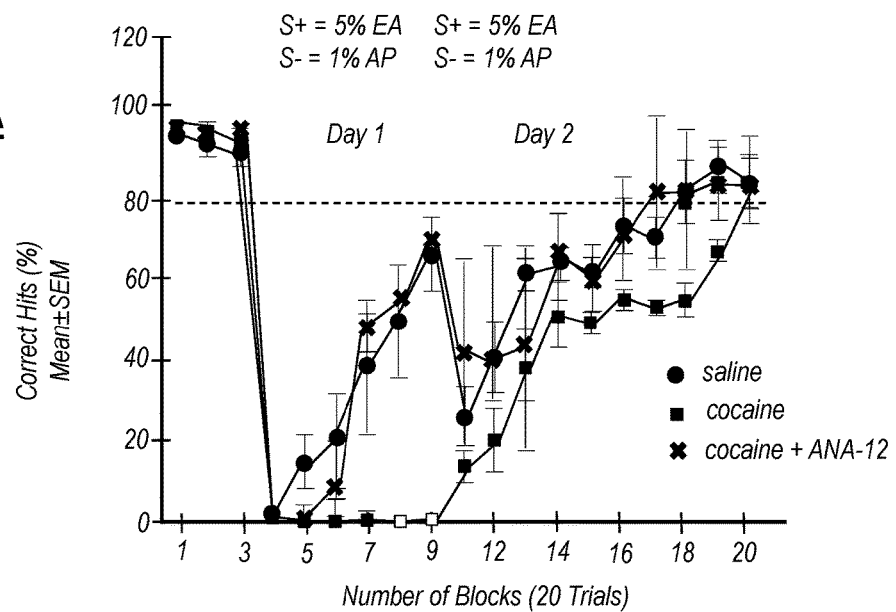
FIG. 2A is a line graph comparison of reversal learning results on prenatally saline- and cocaine-exposed mice vs. prenatally cocaine-exposed mice injected with ANA-12. The mice injected with ANA-12 performed better than the cocaine-exposed mice not injected with ANA-12 (dashed line=80% correct hits).

Next the mice were tested in the reversal paradigm for their ability to relearn a reinforced task upon switching the reward contingency (upon reversal, the previously S− odor was rewarded and S+ odor was unrewarded). The prenatally saline-exposed mice typically had the ability to learn the reversed paradigm within 240 trials and 40% of the mice in this group reached criteria (FIG. 2A, S+ and S− switched on block 4). In contrast, the prenatally cocaine-exposed mice displayed a striking inability to learn the reversed paradigm even after the full 320 trials over 2 days.

Interestingly, not a single mouse from the prenatally cocaine-exposed group nose poked immediately upon presentation of the reversed paradigm on day one (open circles blocks 8-9), and only 11% of the mice in this group reached criteria on day two (blocks 11-20). Thus, the prenatally cocaine-exposed mice showed a significant inability to learn the reversed paradigm.

To test whether the increase in TrkB signaling played a role in olfactory reversal learning, we administered ANA-12, (i.p. twice a day; 1 mg/kg/day) for 13 consecutive days and evaluated the mice in the olfactory reversal learning paradigm.

Figure 2B:
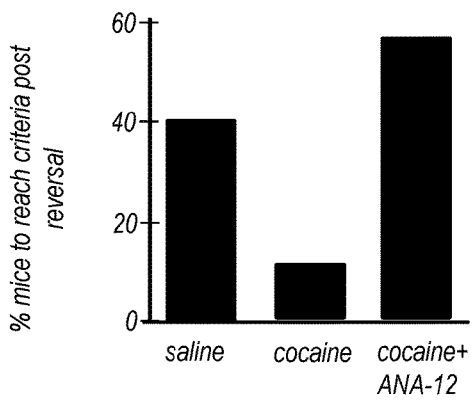
FIG. 2B is a bar graph comparison of the percentage of tested mice that reached performance criteria of at least 80% over the two days.

The ANA-12 exposed mice continued to perform at >80% correct hits in odor versus odor discrimination (data not shown). In striking contrast to the performance of the prenatally cocaine-exposed mice, the ANA-12 treated, prenatally cocaine-exposed mice demonstrated a significant improvement in performance in the reversal paradigm. The ANA-12 injected mice were able to reversal learn over a time course not significantly different than that of saline-exposed mice (Student's t-test; Mean±SEM: Number of trials to reach criteria (≥80%) Saline=210.0±38.7; t=1.128; Cocaine+ANA12=255.0±9.6; t=1.128, df=6, p>0.05). Similar to their saline exposed counterparts, 57% of the ANA-12 injected mice reached criteria (FIG. 2B).

A rank summed test was used to test the efficacy of ANA-12. We compared only saline-exposed (40% reached criteria) and cocaine-exposed mice injected with ANA-12 (57% reached criteria), because only 1 mouse in the cocaine exposed-group met criterion. The medians for saline and cocaine+ANA-12 groups were 250 and 290 respectively. A Mann-Whitney's U test was used to evaluate the difference in the number of trials needed to reach criteria following reversal of the odors. There was no significant difference between the treatment groups (the mean ranks of saline and cocaine+ ANA-12 were 13.5 and 22.5 respectively; U=3.5, p>0.05).

The differences among the three groups of mice [i.e., 1) prenatally saline exposed, 2) prenatally cocaine exposed and 3) prenatally cocaine exposed mice that received ANA-12] were analyzed for statistical significance using two-way ANOVA. Given that the readout for the studies is percentage correct response, a value of zero corresponds to 100% incorrect responses. Therefore, since the prenatally cocaine exposed mice (without ANA-12) did not perform the task at all upon reversal, and the assignment of a value of zero to such performance would not be appropriate (neither correct nor incorrect hits were performed), data for the prenatally cocaine-exposed (non-ANA-12 injected) are notinclude in our analysis.

The statistical analysis was performed in two separate sections: Day 1 (blocks 4-7) and day 2 (blocks 11-20). On day 1, the two-way ANOVA showed a significant main effect of time ($F_{(3,40)}=11.28$, $p<0.0001$), treatment ($F_{(2,40)}=8.14$, $p<0.001$) and interaction ($F_{(6,40)}=3.79$, $p<0.05$). Post-hoc Bonferroni multiple comparison test indicated a significant difference between saline versus cocaine groups (t=3.361, df=40, p<0.01). On day 2, the data analysis showed a significant main effect of time (two-way ANOVA; $F_{(9,124)}=4.31$, $p<0.0001$), treatment ($F_{(2,124)}=3.35$, $p<0.05$) and no significant interaction ($F_{(18,124)}=0.179$, $p<0.05$).

Post-hoc Bonferroni multiple comparison test indicated a significant difference between saline versus cocaine groups (t=3.257, df=124, p<0.01) and cocaine versus cocaine+ ANA-12 groups (t=3.557, df=124, p<0.01; FIG. 2A).

That which is claimed is:

1. A method of treating impaired cognitive flexibility, the method comprising administering to a subject having impaired cognitive flexibility a therapeutically effective amount of a selective tyrosine kinase B (TrkB) receptor antagonist compound, the therapeutically effective amount being sufficient to improve cognitive flexibility in the subject;
   wherein the selective TrkB receptor antagonist compound does not inhibit tyrosine kinase A (TrkA) or tyrosine kinase C (TrkC) receptors;
   wherein the subject is identified as having at least one of attention deficit hyperactivity disorder (ADHD), autism spectrum disorder, and Asperger's syndrome; and
   wherein the TrkB receptor antagonist compound is at least one compound selected from (a) ANA-12, (b) an ANA-12 based compound, and (c) a pharmaceutically acceptable salt of compound (a) or (b), wherein ANA-12 comprises the formula

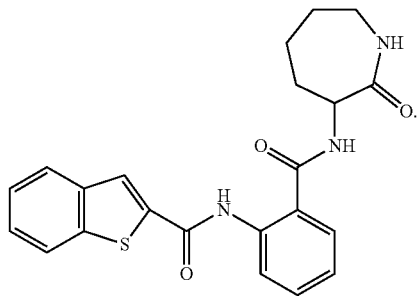 [SMILES: O=C(Nc1ccccc1C(=O)NC1CCCCNC1=O)c1cc2ccccc2s1]

2. The method of claim 1, wherein the subject is identified as having impaired reversal learning.

3. The method of claim 1, wherein the compound is in a pharmaceutical composition including 0.1 to 100 mg of the compound.

4. The method of claim 1, wherein the therapeutically effective amount is 0.001 mg to 20 mg per kg of body weight of the subject.

5. The method of claim 1, further comprising administering a stimulant to the subject.

6. The method of claim 1, wherein the compound is in at least one pharmaceutical dosage form selected from an oral, transdermal, and an injectable dosage form.

7. The method of claim 1, further comprising, prior to administering to the subject having impaired cognitive flexibility the therapeutically effective amount of the selective tyrosine kinase B (TrkB) receptor antagonist compound, conducting a psychiatric evaluation of the patient that determines whether the patient has impaired cognitive flexibility.

* * * * *